US010821037B2

(12) United States Patent
Isele et al.

(10) Patent No.: US 10,821,037 B2
(45) Date of Patent: *Nov. 3, 2020

(54) NONWOVEN THERMAL BONDING PATTERN WITH LOW FUZZ

(71) Applicant: The Procter & Gamble Company, Cincinnati, OH (US)

(72) Inventors: Olaf Erik Alexander Isele, West Chester, OH (US); Donald Raymond Kearney, Springdale, OH (US); Nicole Anja Reichardt, Sulzbach (DE)

(73) Assignee: The Procter & Gamble Company, Cincinnati, OH (US)

(*) Notice: Subject to any disclaimer, the term of this patent is extended or adjusted under 35 U.S.C. 154(b) by 636 days.

This patent is subject to a terminal disclaimer.

(21) Appl. No.: 15/356,711

(22) Filed: Nov. 21, 2016

(65) Prior Publication Data
US 2017/0151102 A1 Jun. 1, 2017

Related U.S. Application Data

(60) Provisional application No. 62/260,733, filed on Nov. 30, 2015.

(51) Int. Cl.
A61F 13/515 (2006.01)
A61F 13/511 (2006.01)
(Continued)

(52) U.S. Cl.
CPC ...... A61F 13/515 (2013.01); A61F 13/15203 (2013.01); A61F 13/513 (2013.01);
(Continued)

(58) Field of Classification Search
CPC ...... D04H 3/14; D04H 13/51476; D04H 1/54; D04H 5/06; D04H 1/4291; D04H 1/544;
(Continued)

(56) References Cited

U.S. PATENT DOCUMENTS 3,616,157 A 10/1971 Smith
3,692,622 A 9/1972 Dunning
(Continued)

FOREIGN PATENT DOCUMENTS

WO WO 00/04215 1/2000
WO WO 01/12427 2/2001
(Continued)

OTHER PUBLICATIONS

International Search Report and Written Opinion, PCT/US2016/060220, dated Jan. 25, 2017.
All Office Actions, U.S. Appl. No. 15/356,705.

Primary Examiner — Elizabeth C Imani
(74) Attorney, Agent, or Firm — Christian M. Best

(57) ABSTRACT

A nonwoven comprising a pattern of thermal bonds with anti-fuzz properties according to at least three and preferably all four of the following conditions: a) the pattern comprises thermal bonds disposed in parallel rows having a pitch angle (P) of from 0.5° to 15° relative to the machine direction or the cross-machine direction; and/or b) the bonding area of all the thermal bonds ranges from 17% to 30% of the area of the nonwoven, and/or c) the pattern comprises larger bonds and smaller bonds having different individual area, and/or d) the pattern comprises elongated bonds having different major directions.

20 Claims, 6 Drawing Sheets

(51) Int. Cl.
*D04H 1/4291* (2012.01)
*D04H 1/544* (2012.01)
*A61F 13/514* (2006.01)
*D04H 5/06* (2006.01)
*D04H 1/54* (2012.01)
*D04H 3/14* (2012.01)
*A61F 13/15* (2006.01)
*A61F 13/513* (2006.01)
*D04H 1/542* (2012.01)
*D04H 1/74* (2006.01)

(52) U.S. Cl.
CPC .. *A61F 13/51108* (2013.01); *A61F 13/51121* (2013.01); *A61F 13/51401* (2013.01); *A61F 13/51476* (2013.01); *A61F 13/51496* (2013.01); *D04H 1/4291* (2013.01); *D04H 1/54* (2013.01); *D04H 1/542* (2013.01); *D04H 1/544* (2013.01); *D04H 1/74* (2013.01); *D04H 3/14* (2013.01); *D04H 5/06* (2013.01); *A61F 2013/15406* (2013.01); *A61F 2013/51377* (2013.01); *A61F 2013/51452* (2013.01)

(58) Field of Classification Search
CPC ........ D04H 1/542; D04H 1/74; A61F 13/515; A61F 13/51108; A61F 13/51476; A61F 13/15203; A61F 13/51121; A61F 13/513; A61F 13/51401; A61F 13/51496; A61F 2013/15406; A61F 2013/51377; A61F 2013/51452

See application file for complete search history.

(56) References Cited

U.S. PATENT DOCUMENTS

| | | |
|---|---|---|
| 5,620,779 A | 4/1997 | Levy et al. |
| 6,286,145 B1 | 9/2001 | Welchel et al. |
| 6,383,958 B1 | 5/2002 | Swanson et al. |
| 6,468,931 B1 | 10/2002 | Reeder et al. |
| 6,620,490 B1 * | 9/2003 | Malchow .................. B32B 7/04 428/196 |
| 8,530,722 B2 | 9/2013 | Rinnert et al. |
| 2004/0241399 A1 | 12/2004 | Marmon et al. |
| 2008/0032579 A1 | 2/2008 | Abed et al. |
| 2012/0156447 A1 | 6/2012 | Hein et al. |
| 2013/0253461 A1 * | 9/2013 | Xu ........................ A61F 13/511 604/384 |
| 2014/0072767 A1 | 3/2014 | Klaska et al. |
| 2018/0025747 A1 | 11/2018 | Bremer et al. |

FOREIGN PATENT DOCUMENTS

| | | |
|---|---|---|
| WO | WO 2014/078247 | 5/2014 |
| WO | WO 2014/200794 | 12/2014 |
| WO | WO 2015/095514 | 6/2015 |

* cited by examiner

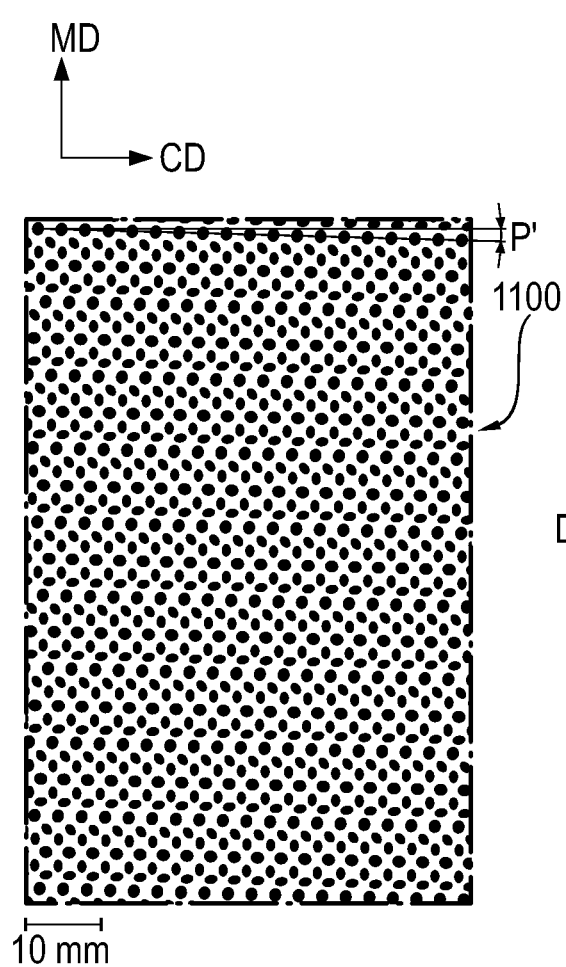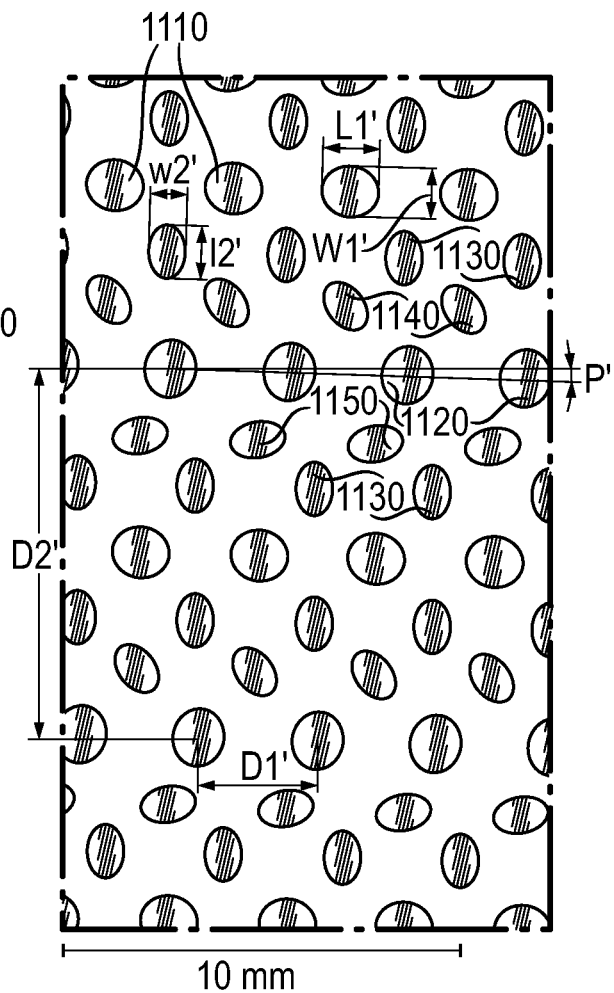
Fig. 11                    Fig. 12
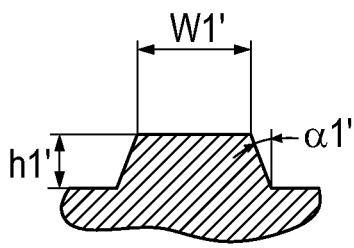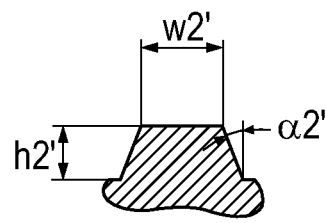
Fig. 13                    Fig. 14

NONWOVEN THERMAL BONDING PATTERN WITH LOW FUZZ

CROSS REFERENCE TO RELATED APPLICATION

This application claims the benefit, under 35 U.S.C. § 119(e), to U.S. Provisional Patent Application Ser. No. 62/260,733, filed on Nov. 30, 2015, which is herein incorporated by reference in its entirety.

FIELD OF THE INVENTION

The invention is directed to an improved thermal bonding pattern for the fibers of a nonwoven. The nonwoven may be used in particular as a topsheet or in a backsheet in absorbent articles such as taped diapers, diaper pants or feminine pads.

BACKGROUND OF THE INVENTION

Absorbent articles for personal hygiene of the type indicated above are designed to absorb and contain body exudates, in particular large quantity of urine. These absorbent articles comprise several layers, typically a topsheet on the wearer-facing side, a backsheet on the garment-facing side and in-between an absorbent core, among other layers. An acquisition and/or a distribution layer may be further provided between the absorbent core and the topsheet. Topsheets are usually either made of a nonwoven or a formed film. Backsheets are typically made of a fluid-impermeable plastic film sometimes doubled on its external side by a nonwoven layer to provide a better feel. It is known to consolidate nonwovens by applying a thermal bonding pattern to the fibers. A commonly used technique involves passing the web of fibers between two calender rolls. One of the roll is typically smooth, and the other roll comprises protrusions having the shape and the disposition of the desired thermal bonding pattern. Typically the calender roll with the protrusion may be heated so that enough heat is applied to the web to locally melt the fibers of the web according to the desired thermal bonding pattern. This and other techniques to provide a bonding pattern on a nonwoven are disclosed in details for example in WO00/04215 (assigned to Fibervisions Inc.).

Various thermal bonding patterns have been suggested. WO01/12427A1 (assigned to First Quality Fibers, Inc) for example discloses a nonwoven with a non-symmetrical bonding configuration. The bonds have a generally oval shape and are oriented in different directions. US2014/0072767 (assigned to Pegas Nowovens S.R.O.) discloses various bonding patterns including convex "wing" shapes and sigmoid "S" shapes. U.S. Pat. No. 8,530,722 (Rinnert et al.) discloses a colored topsheet having a basis weight of from 12 to 18 gsm and comprises a plurality of bonded points. Each of the bonded points has a surface area of from 2 mm$^2$ to 5 mm$^2$ and the cumulated surface area of the plurality of bonded points is from 10 to 25% of the total surface area of the top sheet. The bond points exemplified are generally round and have all the same shape.

The present inventors have found that many of the patterns of the prior art exhibit a relatively large amount of broken fibers that stick out of the surface of the nonwoven, referred to as fuzz. These broken fibers are generally undesirable as they reduce the quality perception of the nonwoven. The inventors believe that breakage may be in particular caused by the abrasion of the nonwoven during wear against the skin or the clothes of the wearer. The abrasion may be principally suffered in the front-to-back direction of the nonwoven i.e. typically the machine direction (MD) of the nonwoven.

SUMMARY OF THE INVENTION

The invention is directed to a nonwoven extending in a machine direction (MD) and a perpendicular cross-machine direction (CD). The nonwoven comprises a pattern of thermal bonds having at least three and advantageously all four of the following characteristics:
  a) the pattern comprises thermal bonds disposed in parallel rows having a pitch angle (P) of from 0.5° to 15° relative to the machine direction or the cross-machine direction; and/or
  b) the bonding area of all the thermal bonds ranges from 17% to 30% of the area of the nonwoven, and/or
  c) the pattern comprises larger bonds and smaller bonds having different individual areas, and/or
  d) the pattern comprises elongated bonds having different major directions.

The inventors have found that the combination of these features can reduce the length of the broken fibers sticking out of the plane of the nonwoven (fuzz). Although not wishing to be bound by theory, the inventors believe that the fibers in the nonwoven, although seemingly randomly aligned, still have a tendency to align in machine direction (MD), i.e. the direction of the production of the web. The inventors believe that if these generally MD-aligned fibers are not sufficiently bonded, in particular if too many MD-oriented bond free "channels" are present, breakage of the fibers in these channels can disproportionally increase the fuzz on the nonwoven. The invention provides an efficient bonding pattern for the fibers of the nonwoven resulting in smaller broken fibers sticking out of the plane of the nonwoven ("fuzz") while keeping desirable attributes such as softness, flexibility, integrity, absorbency and cost-effectiveness.

This and other aspects of the invention is further described and illustrated in the following description and accompanying drawings.

BRIEF DESCRIPTION OF THE DRAWINGS

FIG. 11 shows another exemplary thermal bonding pattern at a scale 1:1 according to the invention;

FIG. 12 shows a close-up of the bonding pattern of FIG. 1 at a scale 5:1;

FIG. 13 is a schematic cross-section of a protrusion of a calender roll for the larger bonds of FIG. 11 at a scale 10:1;

FIG. 14 is a schematic cross-section of a protrusion of a calender roll for the smaller bonds of FIG. 11 at a scale 10:1.

DETAILED DESCRIPTION OF THE INVENTION

Introduction

Figure 1:
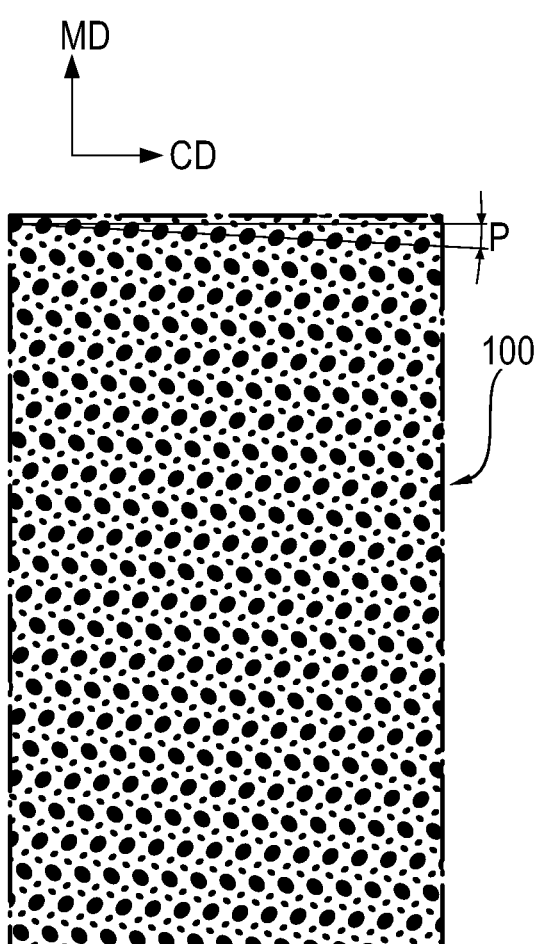
FIG. 1 shows of an exemplary thermal bonding pattern at a scale 1:1 according to the invention.

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Nonwovens

The nonwovens comprising the thermal bonds of the invention may be according to any types of nonwovens known in the art. The term nonwoven typically refers to a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to more than 0.2 mm and they come in several different forms such as short fibers (known as staple, or chopped), continuous single fibers (filaments or monofilaments), untwisted bundles of continuous filaments (tow), and twisted bundles of continuous filaments (yarn).

Nonwoven webs can be formed by many processes such as meltblowing, spunbonding, solvent spinning, electrospinning, carding and airlaying. Nonwovens are typically continuously made by depositing and entangling the fibers on a moving web support. The direction of production of the web is the machine direction (MD), and the direction perpendicular is referred to as the cross-machine direction (CD). The machine direction is the direction along which the web is continuously formed, for example by a spunbonding process, as is known in the art. The machine direction is the continuous or "long" direction of the web, along which the web may be rolled in a roll before being converted in an absorbent article's converting line. The machine direction of the web is thus typically the same direction as the longitudinal direction of the finished article in which the nonwoven is incorporated. The thermal bonding pattern is typically applied to the nonwoven web immediately after the nonwoven web has been formed. The properties of the webs such as strength and stretchability may typically be different when measured in MD or CD. The thermal bond pattern may be typically directly applied after the deposition of the fibers, in particular but not limited to, by passing the nonwoven between two calender rolls.

The basis weight of nonwoven webs is usually expressed in grams per square meter ($g/m^2$ or gsm). The nonwovens of the invention may have any usual basis weight, for example the basis weight may range from 10 gsm to 30 gsm, in particular form 12 gsm to 20 gsm. This range may be particularly useful for a topsheet in an absorbent article, as it provide a good compromise between functionality and economy of material. The basis weight may of course be lower than 10 gsm or higher than 30 gsm for other applications or if other considerations are present. The nonwoven may also be used in other layers of an absorbent article, for example the outer cover of the backsheet. An absorbent article typically comprises a topsheet on its wearer-facing side, a backsheet on its garment-facing side and an absorbent core between the topsheet and the backsheet, and optionally an acquisition layer between the topsheet and the core, as well as longitudinally extending barrier leg cuffs which may be elasticized to prevent side leakage. Any of these layers may comprise a nonwoven according to the invention. Exemplary disclosure of absorbent articles are for example included in WO2014/200784A1 (Bianchi et al.), WO2015/095514 (Laveeta).

In a further aspect, the nonwoven may be colored, e.g. by introducing a pigment in the fibers comprising the nonwoven and/or the nonwoven may have an opacity index of from 15% to 50% as measured by the test described herein. The nonwoven may in particular be used as a topsheet above another layer such as an acquisition layer comprising a visual signal, for example as disclosed in WO2014/078247A1 (Rosati, et al). It was found that the larger thermal bonds may be more relatively transparent and improve the visibility of the visual signal. This was found to be especially the case when the topsheet was made of multilobal fibers, in particular trilobal fibers, as exemplarily disclosed in US2008/0032579A1 (Abed at al.).

General Description of the Pattern Formed by the Thermal Bonds

The invention comprises a pattern of thermal bonds as indicated in the claims defined by the combination of at least three and advantageously four characteristics. The inventors have found that by combining different design features for the thermal bond pattern, the nonwoven obtained can have a lower tendency to fuzz while keeping other required properties such as softness, integrity and absorbency (for a topsheet). The different characteristics of the pattern that can be combined will be discussed individually in the following, and will be further exemplified with reference to the Figures. Each type of bonds present in the pattern may be generally defined by its size (individual area), shape and orientation.

Figure 3:
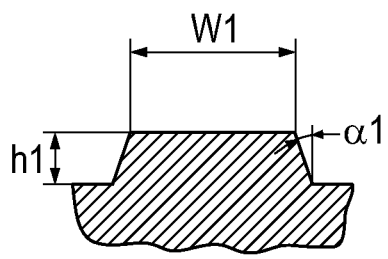
FIG. 3 is a schematic cross-section of a protrusion of a calender roll for the larger bonds at a scale 10:1.
Figure 4:
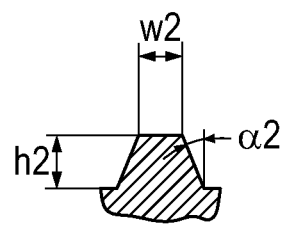
FIG. 4 is a schematic cross-section of a protrusion of a calender roll for the smaller bonds at a scale 10:1.
Figure 5:
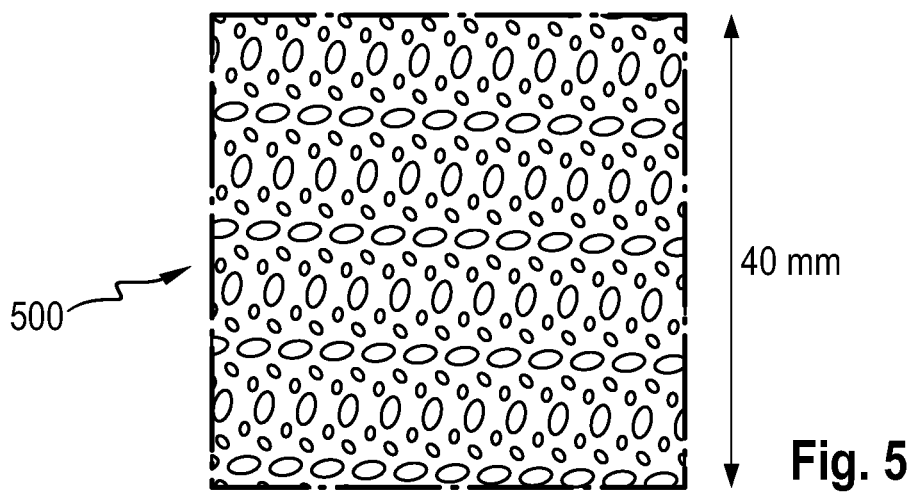
FIGS. 5-10 show different alternative exemplary bonding patterns.
Figure 6:
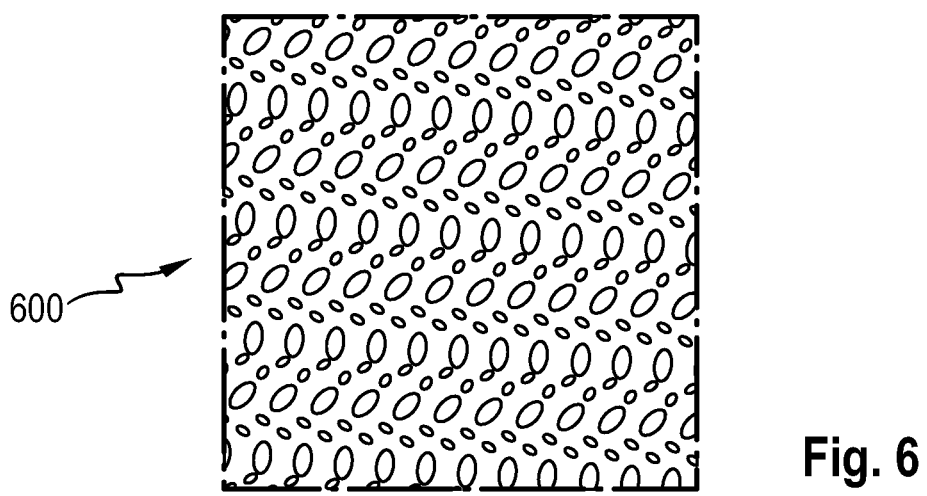
Figure 7:
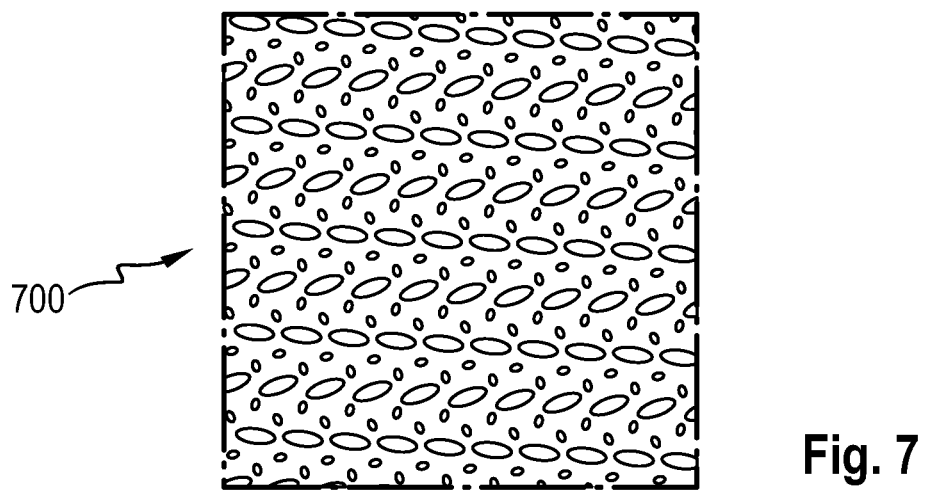
Figure 8:
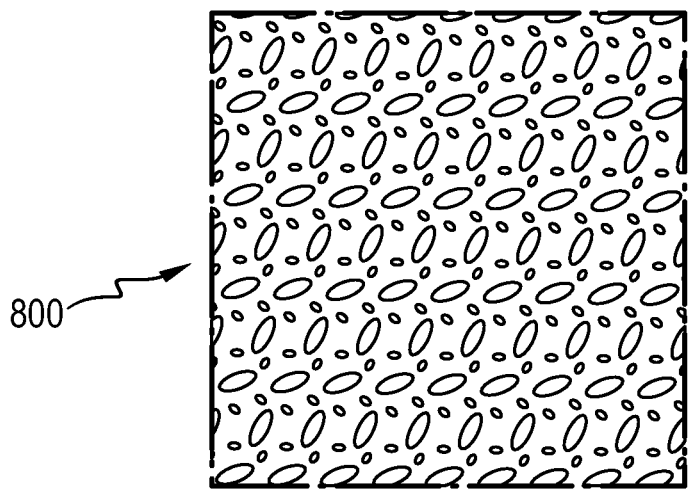
Figure 9:
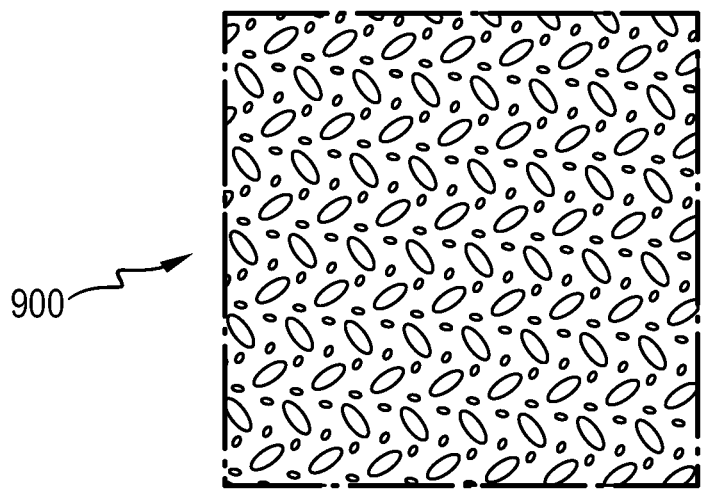
Figure 10:
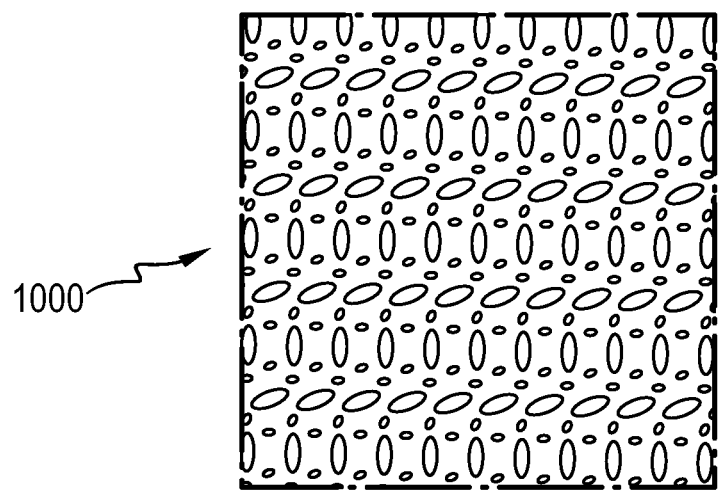
Figure 15:
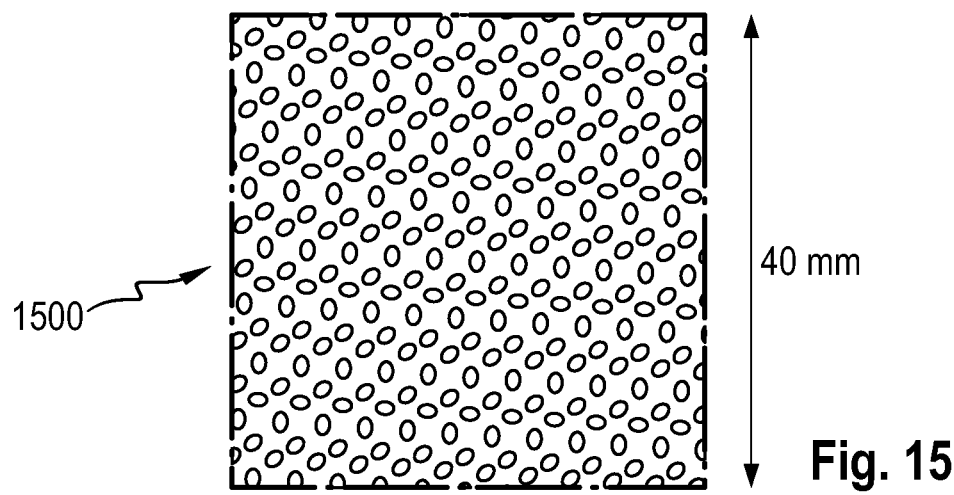
FIGS. 15-19 show further different alternative exemplary bonding patterns.
Figure 16:
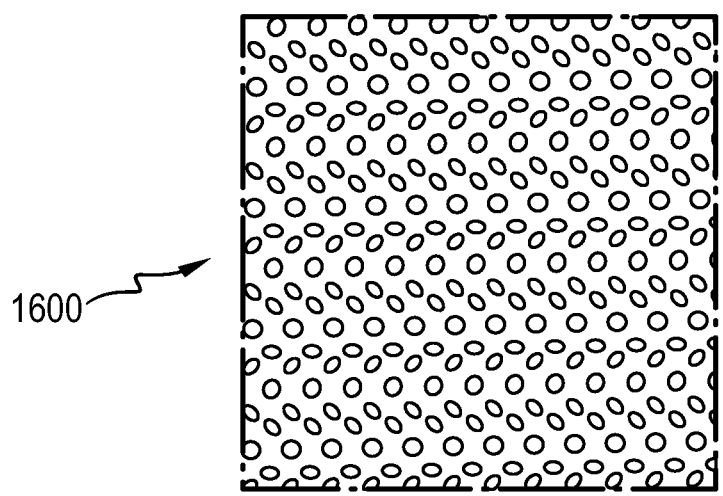
Figure 17:
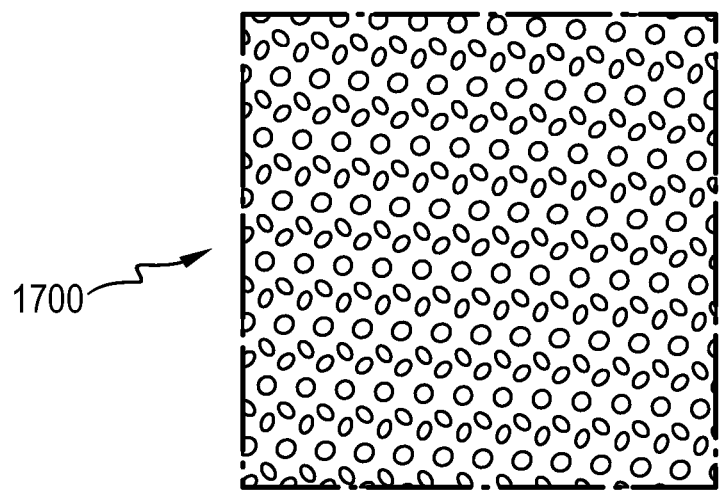
Figure 18:
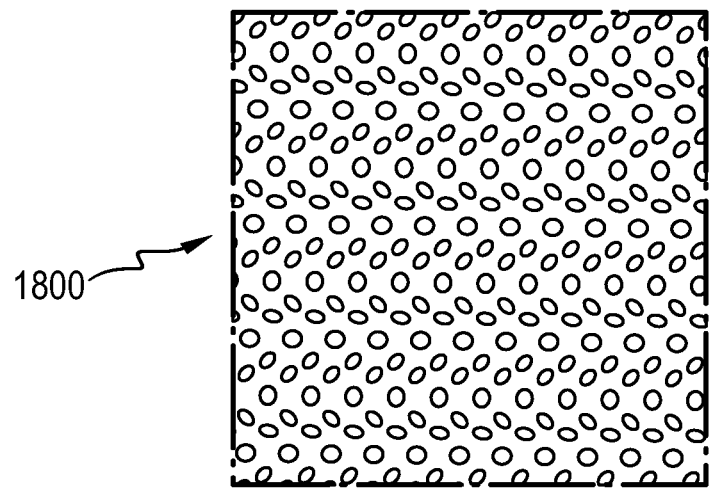
Figure 19:
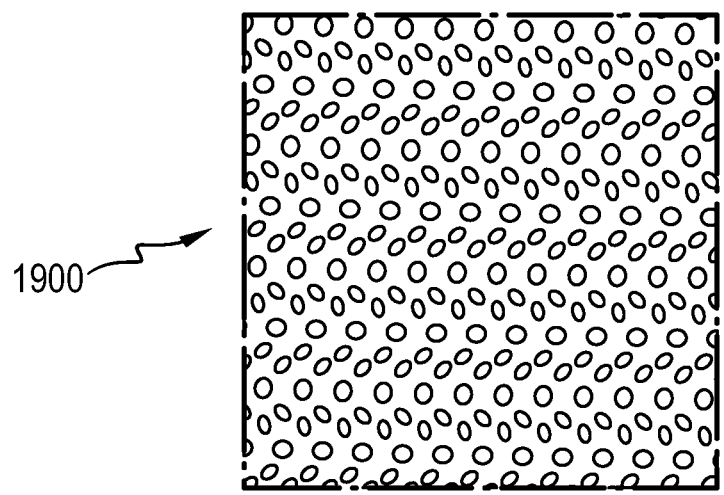

The thermal bonds pattern, including shape, size and orientation of the bonds, is typically determined by the tool used to form the bonds on the nonwoven. As indicated previously, thermal bonds are typically provided on a nonwoven by passing the web of fibers directly after its formation between two calender rolls. Typically, one of the calender rolls will comprise protrusions corresponding to the desired bonding pattern. FIGS. 3 and 4 for example show cross-sections of two protrusions on the calender rolls. The size and shape of the individual bonding points corresponds to the size and shape of the flat, plateau-shaped upper surface of the protrusions. The individual sizes of the thermal bonds can be most easily determined by considering the technical drawings for the calender tool (or other tool used to emboss the thermal bonds, the present invention not being limited to thermal bonds obtained by calender rolls). Typically, technical drawings indicating the dimensions including the individual surface areas of the different thermal bonds will be generated by or for the tool manufacturer to engrave the desired pattern on the calender roll. Alternatively, it is also possible to measure the dimensions of the protrusions of the calender roll, or any other tools used to make the thermal bonds. Finally, if the technical drawings and the bonding tool are not directly available, the size, shape and orientation of the individual bonds may be directly measured on the nonwoven as an end product, for example using microscopic pictures and standard image analysis software.

a) Bonds Disposed in Parallel Rows Having a Pitch Angle (P)

The pattern may advantageously comprises thermal bonds disposed in parallel rows having a pitch angle (P) of from 0.5° to 15° relative to the machine direction (MD) or the cross-machine direction (CD) of the nonwoven. All of the thermal bonds may be disposed in such rows, but it is not excluded that a minority, for example less than 20%, or less than 10% of the bonds, are not aligned in any rows. In the examples further discussed below, the rows are generally aligned parallel to the cross-machine direction taken into account the pitch angle, but the rows may also be generally aligned parallel to the machine direction. By "generally aligned" with the CD or MD, it is meant that the rows have a pitch angle (P) ranging from 0.5 to 15 degrees relative to the CD or MD direction, in particular from 1 to 10 degrees, or from 1 to 5 degrees. Having such a pitch angle ensure that the bonds in consecutive rows are not perfectly aligned with the machine direction. Additionally, it is advantageous that the bonds in two adjacent rows are not aligned in machine direction, but rather that the bonds in consecutive rows are staggered so that the bonds are maximally disrupting or "breaking" the MD oriented bond-free "channels" between the bonds.

In general, all the bonds in a row may be of the same type as defined by size, shape and orientation, but it is not excluded that in some or all the rows, bonds of different types may be present. When the pattern comprises smaller and larger bonds, the distance between two repeating rows having the same type of larger bonds (repeat in height D2) may for example range from 4.0 mm to 16 mm. The distance between two adjacent rows of the larger bonds of different orientation (repeat in height D2/2) may for example range from 2.0 mm to 8 mm. The smaller bonds may then be disposed between the rows of larger bonds. There may be for example two rows of smaller bonds between two rows of larger bonds. The distance center-to-center of two adjacent bonds in a given row (repeat in width D1) may for example range for at least some of the bonds from 2 mm to 8 mm, in particular from 3 mm to 7 mm.

b) Total Bonding Area

The bonding area of all the thermal bonds of the pattern may advantageously represent from 17% to 30% of the area of the nonwoven on which the pattern is applied, in particular from 19% to 28%, more particularly from 21% to 26% of the area of the nonwoven. These ranges were found to provide the optimum anti-fuzz benefits while retaining the softness attribute of the nonwoven. The average amount of thermal bonds (all included) per unit of surface may in particular range from 5 per $cm^2$ to 58 per $cm^2$, in particular from 10 per $cm^2$ to 30 per $cm^2$, but other values are not excluded. All these values are measured of course on a sufficiently large area of the nonwoven to be representative of the pattern as a whole.

c) Bonds Having Different Individual Areas

The pattern of thermal bonds may advantageously comprise bonds having different individual areas, referred herein as larger bonds and smaller bonds. If the bond pattern comprises only two different sizes of bonds (as will be the case for the examples of the Figures), the larger bonds are those having the larger individual area and the smaller bonds are those having the smaller individual area. The larger thermal bonds may all have the same size and shape, and the smaller bonds may also all have the same size and shape. All bonds having the same size may all have the same orientation, but advantageously bonds having the same size and shape may also have different orientation, in particular there may be two types of larger bonds having two different orientations and/or there may be two types of smaller bonds having two different orientations. In case of a more complex pattern comprising bonds having more than two areas, the larger bonds may be defined as those having an area equal or superior to the arithmetic average size of all the bonds, and the smaller bonds are those having an area inferior to the arithmetic average size of all the bonds.

The larger bonds may be alternatively also defined as those bonds having an individual area of at least 1.5 $mm^2$. The larger bonds may be further more restrictively defined as thermal bonds having an individual area of at least 1.5 $mm^2$ or more than 2.0 $mm^2$. There is no maximum size for the larger bonds, but in general the bonds may have an individual area of less than 10 $mm^2$. It is however not excluded that more complex bonding patterns may be used, in particular wherein the pattern comprises more than two sizes of bonds. The larger bonds are advantageous to provide the web with an improved integrity by bonding a large amount of fibers. The larger bonds are typically visually recognizable at the surface of the nonwoven. For example the user of an absorbent article having a topsheet according to the invention may typically recognize the presence of the larger bonds. The smaller bonds may also be alternatively defined has those bonds having an individual area of less than 1.5 $mm^2$, in particular having an individual area of from 0.10 $mm^2$ to less than 1.5 $mm^2$. It is however not excluded that the smaller and larger bonds have other values as indicated previously.

It was found that the smaller bonds help disrupting the channel-like bond-free areas between the larger bonds. It is believed that the smaller bonds can thus considerably reduce the occurrence of long broken fibers from sticking out of the surface of the nonwoven (fuzz). Whereas having only larger bonds may not be desirable, as the overall softness of the nonwoven may be decreased if too many larger bonds are present, it was found however that having smaller thermal bonds in addition to fewer larger bonds did not provide a noticeable softness disadvantage.

The bonding pattern may advantageously comprise at least as many smaller bonds as larger bonds. The ratio of the count of smaller bonds to the count of the larger bonds on a representative area of the nonwoven may be in particular at least 1.2 (i.e. there are 20% more smaller bonds than larger bonds on a count basis), in particular the count ratio may be at least 1.5, more particularly 2.0 or more (i.e. 100% or more smaller bonds than larger bonds). In the examples shown in the Figures discussed further below, there are twice as many smaller bonds than larger bonds (so a ratio of 2:1). However when the individual sizes of the smaller bonds is much smaller than the larger bonds, the larger bonds may still typically provide the largest overall bonding area on the nonwoven. The proportion of the smaller bonds relative to the larger bonds can be simply assessed by selecting a representative surface of the nonwoven and counting how many of each of the bonds are present. This may be expressed in numbers of bonds per unit of surface, per square centimeter for example. Since the ratio of the number of the smaller bonds to the larger bonds is then calculated, the unit of surface is not critical. The information may also be more simply directly read from the technical drawings used to make the tool such as the calendar roll if these are available.

When the pattern comprises elongated bonds of different sizes, the major dimension (L1) of the larger bonds may be in particular at least 50% higher than the major dimension (l1) of the smaller bonds. The major dimension of the larger bonds may in particular be at least 1.50 mm, or at least 1.75 mm, or at least 2.00 mm, and the major dimension of the smaller bond may be less than 1.50 mm, in particular less than 1.25 mm, or less than 1.00 mm. The minor dimension of the larger bonds (W1) may for example range from 0.9 mm to 3.6 mm and the minor dimension (w2) of the smaller bonds may for example range from 0.26 mm to 1.0 mm. At least some of the larger elongated thermal bonds may have a ratio of the major dimension to the minor dimension ranging from 1.05 to 2.0, and at least some of the smaller elongated thermal bonds have a ratio of the major dimension to the minor dimension ranging from 1.10 to 2.5.

d) Elongated Bonds Having Different Major Directions.

The shape of the thermal bonds may be generally rounded, without sharp angle, as in a circle or an oval, and may be particularly elongated featuring a preferred direction of maximal length. These elongated bonds may have in particular a major dimension (i.e. length) measured along a major direction and a minor dimension (i.e. width) measured along a minor direction perpendicular to the major direction. Advantageously, the pattern comprises at least two types of bonds having different major direction (i.e. different orientation). The pattern may comprise in particular bonds having at least three different orientations, more particularly four different orientations. For example, when the pattern comprise elongated larger bonds and elongated smaller bonds, the larger bonds may comprise two or more types of larger bonds having different major directions and the smaller bonds may comprise two or more types of smaller bonds having different major directions.

The larger bonds may thus comprise differently oriented larger bonds, in particular wherein the angle formed by the major dimensions of the differently oriented larger bonds is at least 20°. The smaller bonds may also comprise differently oriented smaller bonds, in particular wherein the angle formed by the larger dimensions of the differently oriented smaller bonds is at least 20°.

At least some of the elongated bonds may have their major direction oriented at an angle of at least 10° relative to the machine direction (MD) of the nonwoven, and preferably more than 10° for example from 15° to 90°. This provides for an increased reduction of the width of MD-oriented bond-free channels between the thermal bonds as discussed above. It is further possible that less than 20% of the total number of the thermal bonds, in particular less than 10% of all the thermal bonds are oriented parallel to the machine direction. There may also be no thermal bonds oriented in the machine direction. All angles are reported herein in absolute value (it is irrelevant whether they are measured clockwise or anti-clockwise). Similarly, all the patterns discussed herein can be duplicated as a reflection across the MD axis or a reflection across the CD axis and these reflections are expected to give the same fuzz reducing result.

The invention will now be further illustrated with reference to the examples as described in the Figures. For ease of discussion, the nonwoven and the thermal bonds may be discussed with reference to the numerals referred to in these Figures. However it should be understood that these exemplary embodiments and the numerals are not intended to limit the scope of the claims, unless specifically indicated. Nothing in this description should be considered limiting the scope of the claims unless explicitly indicated otherwise.

EXAMPLES

Figure 2:
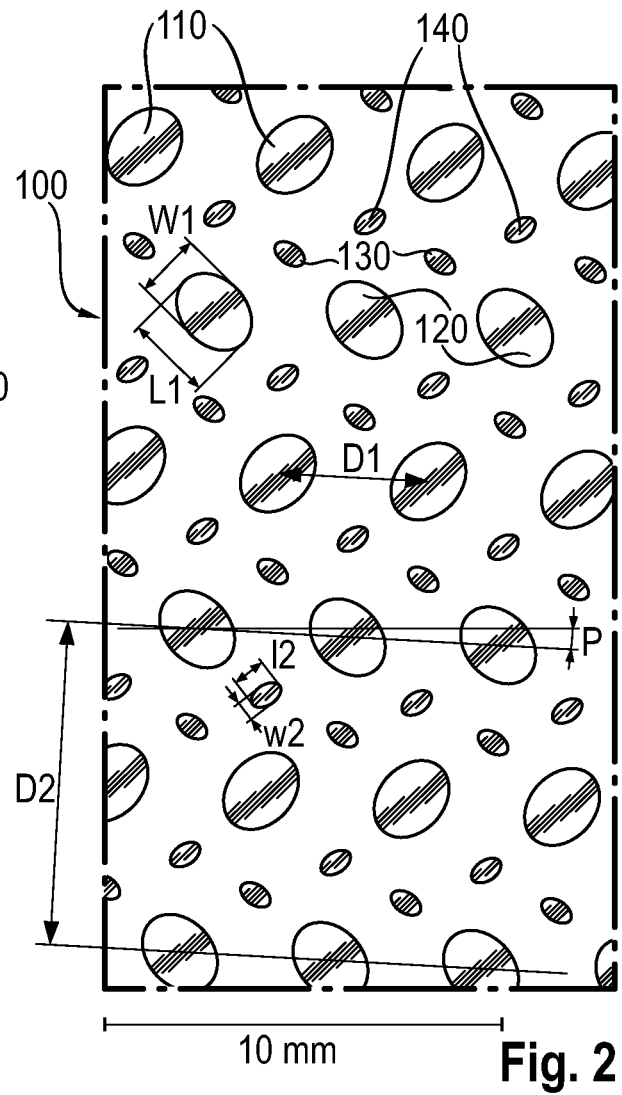
FIG. 2 shows a close-up of the bonding pattern of FIG. 1 at a scale 5:1.

FIG. 1 illustrates a bonding pattern 100 for a nonwoven having thermal bonds of different sizes and orientations. FIG. 1 is at a scale of 1:1, while FIG. 2 is a close-up view at a scale of 5:1. The nonwoven extends in a machine direction (MD) and a perpendicular cross-machine direction (CD). This bonding pattern is discussed below for the purpose of illustration. The general considerations indicated above may of course be applied to modify the exemplified designs. For example in the example of FIGS. 1-2, the individual area of the larger bonds 110, 120 is 3.2 mm$^2$ and the individual area of the smaller bonds 130, 140 is 0.36 mm$^2$, and there are twice as many smaller bonds than larger bonds, but the ranges indicated previously may be applied to modify any of these values. The larger bonds on one hand and the smaller bonds on the hand may have the all same individual areas as shown. Of course it is not excluded that the larger and/or the smaller bonds have different areas within the range indicated. It is also not excluded that other bonds are present that are neither large or small as defined in the claims. The bonding pattern 100 may comprise at least three, in particular four or more different types of bonds 110-140, wherein each type of bonds is defined by size, shape and orientation of its major direction.

The bonding pattern 100 illustrated in FIGS. 1-2 comprises larger bonds 110, 120 and smaller bonds 130, 140. All the bonds have a generally rounded (in particular elliptical) shape, with no sharp angles. As can be better seen on FIG. 2, the larger bonds comprise two types of larger bonds, wherein the first type 110 and the second type 120 of larger bonds are orientated in a different major directions while having the same size and shape. Similarly, the smaller bonds 130, 140 comprise a first type of smaller bonds 130 and a second type of smaller bond 140, having the same size and shape but oriented in different directions. In FIGS. 1-2, the bonds having the same size but having different orientations are symmetrically oriented relative to the machine direction, in particular they may be placed with their major direction being about perpendicular to each other (at an angle of about 90°). More generally, when the larger bonds comprise differently oriented larger bonds 110, 120, the angle formed by the major dimensions of the differently oriented larger bonds may be for example at least 20°, or at least 45° and thus up to 90°. Similarly, when the smaller bonds comprise differently oriented smaller bonds, these may be symmetrically oriented relative to the machine direction. The angle formed by the major dimensions of the differently oriented smaller bonds may be for example at least 20°, or at least 45° and thus up to 90°.

The larger bonds 110, 120 have a major dimension L1 measured along a major direction and a minor dimension W1 measured along a minor direction perpendicular to the major direction, and smaller elongated thermal bonds 130, 140 having a major dimension l2 measured along a major direction and a minor dimension w2 measured along a minor direction perpendicular to the major direction.

The thermal bonds represented in the FIGS. 1-2 comprise a sub-pattern of six repeating rows, each row generally orientated parallel to the cross-machine direction, taking into account an optional but preferred pitch angle P. Each row may comprise a single type of thermal bonds having the same size, shape and orientation. As indicated previously, the pitch angle P measures the angle between the rows and the cross-machine direction (CD), and may typically range from 0.5 to 15 degrees relative to the CD direction (alternatively the MD). Having a non-zero pitch angle improves the properties of the bonding pattern by ensuring two consecutive rows of the same type of bonds are slightly shifted in CD direction. This can further improve the anti-fuzz properties of the bonding pattern. Although not illustrated, the pattern may also comprise rows generally oriented in MD having the pitch angle relative to MD. The repeat in width distance center-to-center D1 of two adjacent bonds in a given row may be, as illustrated, the same distance for all the bonds in a given row. The repeat in height distance D2 between two rows of bonds of the same type may also be the same for all the rows, as in illustrated in the Figures. It is not excluded that other bonding pattern may have different repeat value in CD or MD although having the constant values for all the bonds of the same type may be simpler.

The following table summarizes the main dimension of the example of FIGS. 1-2, further indicating broader ranges in which the values may be modified as indicated in the general disclosure section above.

TABLE 1

Exemplary values for the dimension for the pattern of FIGS. 1-2

| Dimension | Value in FIGS. 1-2 | Indicative range |
|---|---|---|
| Ratio of the number of smaller bonds/larger bonds | 2:1 | 1 to 3 |
| Larger bond's area 110, 120 | 3.2 mm$^2$ | 1.5 mm$^2$-10 mm$^2$ |
| Smaller bond's area 130, 140 | 0.36 mm$^2$ | 0.10 mm$^2$ to <1.5 mm$^2$ |
| Larger bond's length L1 | 2.25 mm | at least 1.50 mm |
| Smaller bond's length l2 | 0.88 mm | less than 1.50 mm |
| Ratio L1/l2 | 2.56 | L1/l2 ≥ 1.5 |
| Larger bond's width W1 | 1.8 mm | 0.9 mm-3.6 mm |
| Smaller bond's width w2 | 0.52 mm | 0.26 mm-1.0 mm |
| Repeat in width D1 | 4.1 mm | 2 mm-8 mm |
| Repeat in height D2 | 8.6 mm | 4.0 mm-16 mm |
| Pitch angle p = | 3° | 0.5-10° |
| Total number of bonds/cm$^2$ | 17 | 5-58 |
| Bonded area | 22.1% | 17%-30% |

The pattern of thermal bonds shown can obtained by passing a nonwoven web through two calendaring rolls, at least one of the calendaring rolls having bonding protrusions. The protrusions are illustrated by FIGS. 3 and 4 showing cross-sections of the larger and smaller protrusions in their minor directions at a scale of 10:1. FIG. 3 illustrates a protrusion for providing the larger thermal bonds 110, 120, while FIG. 4 illustrates a protrusion for providing the smaller thermal bonds 130, 140. The protrusions have a height h1, h2 (also referred to as engraving depth), with typically h1 being equal to h2, and the side walls of the protrusions extend from the surface of the roll at angles α1, α2, with typically a1 being equal to α2. In the specific example shown, h1=h2=0.68 mm, α1=α2=22°.

In a first application example, polypropylene pigmented trilobal fibers comprising 0.3% TiO2 (by weight of the web) were formed into a web of fibers at a basis weight of 12 gsm using the spunbond process. The web was then immediately passed between calender rolls with one roll having the bonding pattern as shown in FIGS. 1-2. In a second example, the polypropylene pigmented trilobal fibers comprised 1% TiO2 by weight and the spunbond web had a basis weight of 17 gsm. The second web was also passed through calender rolls with the same bonding pattern. Both resulting nonwovens were used as a topsheet in a baby diaper. A printed signal present on the acquisition layer was clearly visible through the topsheet. Liquid management performance were good (rewet and liquid absorption). The TiO2 particles were introduced as an matting agent to reduce the shine of the nonwoven. The opacity of the first nonwoven was measured at 31% and of the second nonwoven at 45%.

FIGS. 5 to 10 show further examples of bonding patterns 500-1000, that were computer generated. A general description of computer-generated pattern can be created is indicated at the end of this description. These further bonding patterns also comprise larger bonds having all the same size and shape but oriented in two different directions, and likewise for the smaller bonds. The squares shown for FIGS. 5-10 have a side dimension of 40 mm. The exemplary dimensions of the bonds in these patterns are as indicated below in Table 2 below:

TABLE 2

Exemplary values for the dimension for the pattern of FIGS. 5-10

| Dimensions | Pattern 500 | Pattern 600 | Pattern 700-1000 |
|---|---|---|---|
| Ratio of the number of smaller bonds/larger bonds | 2:1 | 2:1 | 2:1 |
| Larger bond's area | 2.8 mm$^2$ | 2.9 mm$^2$ | 3.2 mm$^2$ |
| Smaller bond's area | 0.56 mm$^2$ | 0.48 mm$^2$ | 0.37 mm$^2$ |
| Larger bond's length | 2.6 mm | 2.7 mm | 3.2 mm |
| Smaller bond's length | 1.1 mm | 1.1 mm | 0.9 mm |
| Larger bond's width | 1.4 mm | 1.4 mm | 1.3 mm |
| Smaller bond's width | 0.65 mm | 0.57 mm | 0.52 mm |
| Total number of bonds/cm$^2$ | 17 | 17 | 17 |
| Bonded area | 22.1% | 22.1% | 22.1% |

Further Examples

FIG. 11 illustrates another bonding pattern 1100 for a nonwoven. FIG. 11 is at a scale of 1:1, while FIG. 12 is a close-up view at a scale of 5:1. The nonwoven extends in a machine direction (MD) and a perpendicular cross-machine direction (CD). As for the bonding pattern of FIGS. 1-2, the general considerations indicated above may of course be applied to modify the exemplified designs. The pattern of FIGS. 11-12 comprise two types of larger bonds 1110, 1120 and three types of smaller bonds 1130, 1140, 1150. All the larger bonds have the same individual area. All the smaller bonds also have the same individual area. The difference of sizes of the larger and smaller bonds is however less than in the previous examples, as will be summarized with the other dimensions in Table 3 below.

All the bonds have a generally rounded, in particular elliptical shape, with no sharp angles. As can be better seen on FIG. 12, the larger bonds comprise two types of larger bonds, wherein the first type 1110 and the second type 1120 of larger bonds are orientated in a different major directions, while having the same size and shape. The first type of larger bonds 1110 is generally oriented in MD, and the second type of larger bonds 1120 perpendicular thereto, generally parallel to CD. The smaller bonds comprise a first type of smaller bonds 1130, oriented generally parallel to MD, a second type of smaller bonds 1140 oriented at an angle of about 45° relative to MD and a third type of bonds 1150 oriented at an angle of about 70° relative to MD.

The larger bonds have a major dimension L1' measured along a major direction and a minor dimension W1' measured along a minor direction perpendicular to the major direction, and the smaller elongated thermal bonds have a major dimension 12' measured along a major direction and a minor dimension w2' measured along a minor direction perpendicular to the major direction. The pattern of thermal bonds represented in the FIGS. 11-12 may be defined as a recurring sub-pattern of six rows, each row generally orientated parallel to the cross-machine direction, taking into account the pitch angle P'. Each row comprises a single type of thermal bonds having the same size, shape and orientation. Two of these rows have the same type of bonds 1130 (the smaller bonds oriented generally in MD) so that in total there are five different types of bonds in the pattern.

The repeat in width distance center-to-center D1 of two adjacent bonds in a given row may be, as illustrated, the same distance for all adjacent bonds. The repeat in height distance D2 between two rows of the same type may be also the same for all the rows in the illustrated Figures, except for the rows comprising the smaller bonds 1130 oriented generally in MD, which have repeat height of D2/2 as they repeat twice as often as the other rows. It is not excluded that other bonding pattern may have different repeat value in CD or MD although having the constant values for all the bonds of the same type may be simpler.

The following table summarizes the main dimension of the example of FIGS. 11-12, further indicating broader ranges in which these exemplary values may be modified as indicated in the general disclosure section above. It is noted again that these indicative ranges are not necessary, for example the smaller bond length 12' in the pattern of FIG. 11 is at the outer border of the indicative range.

TABLE 3

Exemplary values for the dimension for the pattern of FIGS. 11-12

| Dimension | Value in FIGS. 11-12 | Indicative range |
|---|---|---|
| Ratio of the number of smaller bonds/larger bonds | 2:1 | 1 to 3 |
| Larger bond's area 1110, 1120 | 1.76 mm$^2$ | 1.5 mm$^2$-10 mm$^2$ |
| Smaller bond's area 1130, 1140 | 1.18 mm$^2$ | 0.10 mm$^2$ to <1.5 mm$^2$ |
| Larger bond's length L1' | 1.6 mm | at least 1.50 mm |
| Smaller bond's length l2' | 1.5 mm | <1.50 mm |
| Larger bond's width W1' | 1.4 mm | 0.9 mm-3.6 mm |
| Smaller bond's width w2' | 1 mm | 0.26 mm-1.0 mm |
| Repeat in width D1' | 3.3 mm | 2 mm-8 mm |
| Repeat in height D2' | 10.3 mm | 4.0 mm-16 mm |
| Pitch angle P' = | 2° ± 0.2° | 0.5-10° |
| Total number of bonds/cm$^2$ | 17.6 | 5-58 |
| Bonded area | 24.2% | 17%-30% |

In a third application example, polypropylene pigmented trilobal fibers comprising 0.3% TiO2 (by weight of the web) were formed into a web of fibers at a basis weight of 12 gsm using the spunbond process. In a fourth application example, the polypropylene pigmented trilobal fibers comprised 1% TiO2 by weight and the spunbond web had a basis weight of 17 gsm. Both webs were immediately passed in calender rolls with one roll having the bonding pattern as shown in FIGS. 11-12. Both resulting nonwovens were used as a topsheet in a baby diaper. A printed signal present on the acquisition layer was clearly visible through the topsheet. Liquid management performance were good (rewet and liquid absorption). The TiO2 particles were introduced as an matting agent to reduce the shine of the nonwoven. The opacity of the 12 gsm nonwoven was measured at 30% and of the 17 gsm nonwoven at 43%.

FIGS. 15 to 19 show further examples of bonding patterns 1500-1900, that were computer generated. These bonding patterns also comprise larger bonds having all the same size and shape but oriented in two different directions, and likewise all the smaller bonds had all the same sizes and different directions. The squares shown for FIGS. 15-19 have a side dimension of 40 mm. The exemplary dimensions of the bonds in these patterns are as indicated below in Table 4 below:

TABLE 4

Exemplary values for the dimension for the pattern of FIGS. 15-19

| Dimensions | Pattern 1500 | Patterns 1600-1900 |
|---|---|---|
| Ratio of the number of smaller bonds/larger bonds | 2:1 | 2:1 |
| Larger bond's area | 1.4 mm$^2$ | 1.7 mm$^2$ |
| Smaller bond's area | 1.2 mm$^2$ | 1.1 mm$^2$ |
| Larger bond's length | 1.6 mm | 1.6 mm |
| Smaller bond's length | 1.5 mm | 1.5 mm |
| Larger bond's width | 1.2 mm | 1.4 mm |
| Smaller bond's width | 1.1 mm | 1.0 mm |
| Total number of bonds/cm$^2$ | 17 | 17 |
| Bonded area | 22.1% | 22.1% |

Test Method: Opacity

Opacity by contrast ratio measurements are made using a 0°/45° spectrophotometer suitable for making standard Hunter L*a*b* color measurements (e.g. Hunterlab Labscan XE spectrophotometer, Hunter Associates Laboratory Inc., Reston Va. or equivalent). The diameter of the instrument's measurement port should be chosen such that only the region of interest is included within the measurement port. Analyses are performed in a room controlled at about 23° C.±2 C.° and 50%±2% relative humidity. Samples are conditioned at the same condition for 2 hours before testing.

Calibrate the instrument per the vender instructions using the standard black and white tiles provided by the vendor. Set the spectrophotometer to use the CIE XYZ color space, with a D65 standard illumination and 10° observer. Using cryogenic spray and scissors excise the topsheet specimen from the article for testing. Place the specimen flat against the instrument with the body facing surface toward the spectrophotometer's measurement port and the region of interest within the port. Place the white standard tile onto the opposing surface of the specimen such that it completely covers the measurement port. Take a reading for XYZ and record to 0.01 units. Without moving the specimen, remove the white plate and replace it with the black standard plate. Take a second reading for XYZ and record to 0.01 units. Repeat this procedure at a corresponding site for a total of ten (10) replicates specimens.

Opacity is calculated by dividing the Y value measured using the black tile as backing, divided by the Y value measured using the white tile as backing, then multiplying the ratio by 100. Record opacity to the nearest 0.01%. Calculate opacity for the 10 replicates and report the average opacity to the nearest 0.01%.

Computer Generated Patterns

Disclosed herein are methods of simulating a bond pattern for nonwovens that allows for the evaluation of mechanical properties and aesthetic properties when used in an absorbent article. The bond pattern may be evaluated pre and post converting. The present disclosure assists in predicting the visual aspect of the bond pattern created by its physical components and how changes in the physical components may impact the consumer during use.

Also included is a computing device that includes a memory component that stores logic that causes the system to receive a computer based simulation of an absorbent article. The logic simulates physical changes within the absorbent article that are controlled by the user of the simulation.

Also included is a non-transitory computer-readable medium that stores a program that when executed by a computing device causes the computing device to receive a computer based simulation an absorbent article. The system then simulates modifications to different physical characteristics of the absorbent article in a three dimensional form. In an embodiment, the system may extract one or more frames of finite element analysis to establish mapping of the physical characteristics and the geometry. Alternatively, the system may determine intermediate states artistically.

Computer aided engineering (CAE) is a broad area of applied science in which technologists use software to develop computer based models that represent real world things. The models can be transformed to provide information about the physical behavior of those real world things, under certain conditions and over particular periods of time. With CAE, the interactions of the computer based models are referred to as simulations. Sometimes the real world things are referred to as a problem and the computer based model is referred to as a solution.

Commercially available software can be used to conduct CAE. ABAQUS, LS-DYNA™ Fluent, from ANSYS™, Inc. in Canonsburg, Pa., Flow3D™, from Flow Science, Inc. in Santa Fe, N. Mex., and FeFlow™ from DHI-WASY in Berlin, Germany are examples of commercially available CAE software. Other commercially available software includes Maya, 3DS Max, Cinema 4D, and Houdini. The current method may also utilize a commercially available 3D runtime engine traditionally used for games or other 3D content presentations such as, for example, Unreal, Crysis, Unity, VirTools, and combinations thereof. ABAQUS™, LS DYNA™, ANSYS™, and MARC™ are examples of commercially available Structural Analysis software. The Structural Analysis software may utilize finite element analysis (FEA). In FEA, models representing mechanical articles, as well as their features, components, structures, and/or materials are transformed to predict stress, strain, displacement, deformation, and other mechanical behaviors. FEA represents a continuous solid material as a set of discrete elements. In FEA, the mechanical behavior of each element is calculated, using equations that describe mechanical behavior. The results of all of the elements are summed up to represent the mechanical behavior of the material as a whole.

Alternatively, CAE software or any derivative such as FEA software can be written as custom software or may be open source code software. FEA and CAE software can be run on various computer hardware, such as, for example, a personal computer, a minicomputer, a cluster of computers, a mainframe, a supercomputer, or any other kind of machine on which program instructions can execute to perform functions.

Graphic rendering relates to the addition of graphics to an image or data structure. The image or data structure may include geometry, viewpoint, texture, lighting, and shading information as a description of the virtual scene. Commercially available graphic rendering tools may be used to simulate the graphics on a package. Such tools include, for example, Maxwell®, Mental Ray® and Vray®.

CAE models utilizing graphic rendering tools can represent a number of real world things, such as an absorbent article either on a user or by itself and all of the physical components of the absorbent article.

The following steps represent a method for generating and rendering a 2-D/3-D model of a bond pattern. The method includes determining a complex bond pattern, animating that bond pattern over an area including designing the shape/layout over a machine direction and a cross direction, running a simulation, and evaluating the simulation.

Determining a complex bond pattern includes creating a bond pattern wherein each bond has a given set of dimensions and an inclination angle. Determining a complex bond pattern may include choosing the materials that are being bonded and also the bonding method. Determining a complex bond pattern may include designing a bond group arrangement, designing the machine direction layout of the bonds, the cross direction layout of the bonds, or the layout of the bonds for both the machine and cross directions. Determining a complex bond pattern may include designing the group machine direction layout of the bonds, the cross direction group layout of the bonds, or the group layout of the bonds for both the machine and cross directions.

Once a bond pattern is determined, the bond pattern may be animated using equations. Further the shape and layout of the bond pattern may be determined by Design of Experiments Methodology.

The bond pattern is then simulated using two dimensional simulation, three dimensional simulations, or both two and three dimensional simulations that may evaluate the model for various aspects including but not limited to the appearance of the bond, the possible creation of fuzz on the surface of the material, compression of the bonded material, the orientation of the bonds, and the creation of dust particles in forming the material edges. The simulation may also evaluate the embossing process for the chosen material, the mechanical properties for the bonded material, the aesthetic properties for the bonded material, the potential for converting the bonded material into a consumer product or a portion of a consumer product, and how the bonded material will affect a final consumer product. If the output is not as desired by the user, the method allows for design changes for any of the parameters discussed above.

The method includes a first step of creating a computer based simulation of a bond pattern for an absorbent article. The computer based model may be created as described below, with general references to a computer based model of the bond pattern. A computer based model that represents the bond pattern may be created by providing dimensions and material properties to the modeling software and by generating a mesh for the absorbent article using meshing software. A mesh is a collection of small, connected polygon shapes that defines the set of discrete elements in a CAE computer based model. It is understood that the shapes may be two-dimensional, three-dimensional, or a combination of both. The type of mesh and/or the size of elements may be controlled with user inputs into the meshing software, as will be understood by one of ordinary skill in the art.

A computer based model of the bond pattern may be created with dimensions that are similar to, or the same as, dimensions that represent parts of a real world absorbent article. These dimensions may be determined by measuring actual samples, by using known values, or by estimating values. Alternatively, a model of an absorbent article bond pattern may be configured with dimensions that do not represent a real world absorbent article. For example, a model of an absorbent article bond pattern may represent a new variation of a real world absorbent article bond pattern or may represent an entirely new bond pattern. In these examples, dimensions for the model may be determined by varying actual or known values, by estimating values, or by generating new values. The model may be created by putting values for the dimensions of parts of the bond pattern into the modeling software.

The computer based model of the absorbent article bond pattern may be created with material properties that are similar to, or the same as, material properties that represent a real world absorbent article. These material properties may be determined by measuring actual samples, by using known values, or by estimating values. Alternatively, a model of an absorbent article bond pattern may be configured with material properties that do not represent a real world absorbent article. For example, a model of a package may represent a new variation of a real world absorbent article bond pattern or may represent an entirely new material. In these examples, material properties for the model may be determined by varying actual or known values, by estimating values, or by generating new values.

The computer based model of the bond pattern may be created with a mesh for the bond surface area. In an embodiment, a surface of the absorbent article may be created by using shell elements, such as linear triangular elements (also known as S3R elements) with an element size of about less than 10 mm such as, for example, less than 5 mm, less than 4 mm, less than 3 mm, less than 2 mm, and 1.5 millimeters. Also, a material may be created by using solid elements, such as linear hexahedral elements (also known as C3D8R elements) with an element size of about 1.5 millimeters.

Many data structures are possible for representing the mesh of the bond pattern. In one embodiment, a data structure for the bond pattern representing the parts by a set of nodes, and for the connected edges, classifying the edges of the polygons into connection nodes, wherein two edges that are in the same connection node have end-points on the same node.

Manipulating the model may include entering different attributes through a user interface. The user interface provides the user with an interactive tool operative to change one or more parameters of the modeled absorbent article bond pattern.

Misc

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven extending in a machine direction and a perpendicular cross-machine direction and comprising a pattern of thermal bonds according to the following:
    a) the pattern comprises thermal bonds disposed in parallel rows, the rows having a pitch angle of from about 0.5° to about 15° relative to the machine direction or the cross-machine direction;
    b) a bonding area of all the thermal bonds covers from about 17% to about 30% of an area of the nonwoven;
    c) the pattern comprises elongated larger bonds and elongated smaller bonds and having different individual areas, wherein at least some of the elongated larger bonds are disposed in the parallel rows, wherein at least some of the elongated smaller bonds are disposed in the parallel rows, wherein a ratio of the number of the elongated smaller bonds to the number of the elongated larger bonds is at least 1.5, and wherein at least some of the parallel rows of the elongated smaller bonds are disposed between at least some of the parallel rows of the elongated larger bonds; and
    d) wherein the elongated smaller and larger bonds have a rounded shape and have a major dimension measured along a major direction and a minor dimension measured along a minor direction perpendicular to the major direction, wherein at least some of the elongated smaller and larger bonds have a major direction which is not oriented parallel to the machine direction, and wherein the elongated smaller and larger bonds have different major directions.

2. The nonwoven according to claim 1, wherein the pitch angle of the parallel rows ranges from about 1° to about 10° relative to the cross-machine direction.

3. The nonwoven according to claim 1, wherein the distance between two adjacent parallel rows of the elongated larger bonds is from about 2.0 mm to about 8 mm and a distance center-to-center for at least some of the elongated larger bonds in the same parallel row ranges from about 2 mm to about 8 mm.

4. The nonwoven according to claim 1, wherein the bonding area of all the thermal bonds ranges from about 19% to about 28% of the area of the nonwoven.

5. The nonwoven according to claim 1, wherein the elongated smaller bonds have an individual area in the range of 0.10 mm$^2$ to 1.5 mm$^2$, and wherein the elongated larger bonds have an individual area of at least 1.5 mm$^2$.

6. The nonwoven according to claim 5, wherein the ratio of the number of elongated smaller bonds to the number of elongated larger bonds is at least 2.0.

7. The nonwoven according to claim 1, wherein the pattern comprises larger elliptical shape bonds and smaller elliptical shape bonds, wherein the major dimension of the larger elliptical shape bonds is at least 2.0 mm, and wherein the major dimension of the smaller elliptical shape bonds is less than 1.0 mm.

8. The nonwoven according to claim 7, wherein at least some of the larger elliptical shape bonds have a ratio of the major dimension to the minor dimension ranging from about 1.05 to about 2.0, and wherein at least some of the smaller elliptical shape bonds have a ratio of the major dimension to the minor dimension ranging from about 1.10 to about 2.5.

9. The nonwoven according to claim 1, wherein the pattern of thermal bonds comprises elliptical shape bonds that have a major dimension measured along a major direction and a minor dimension measured along a minor direction perpendicular to the major direction, and wherein at least some of the elliptical shape bonds have a major direction which is not oriented parallel to the machine direction.

10. The nonwoven according to claim 9, wherein at least some of the elliptical shape bonds have their major directions oriented at an angle of at least 15° relative to the machine direction of the nonwoven.

11. The nonwoven according to claim 1, wherein the pattern comprises larger elliptical shape bonds and smaller elliptical shape bonds having different individual areas, and wherein
the larger elliptical shape bonds have a major dimension measured along a major direction, and a minor dimension measured along a minor direction perpendicular to the major direction;
the smaller elliptical shape bonds have a major dimension measured along a major direction, and a minor dimension measured along a minor direction perpendicular to the major direction; and
wherein the major dimension of the larger elliptical shape bonds is at least 50% higher than the major dimension of the smaller elliptical shape bonds.

12. The nonwoven according to claim 1, wherein an angle formed by the major directions of the differently oriented larger bonds is at least 20°.

13. The nonwoven according to claim 1, wherein at least some of the elongated smaller bonds have different major directions, and wherein an angle formed by the major directions of the differently oriented elongated smaller bonds is at least 20°.

14. The nonwoven according to claim 1, having a basis weight ranging from about 10 gsm to about 30 gsm and an opacity index of from about 15% to about 50%.

15. An absorbent article comprising:
a topsheet on a wearer-facing side of the absorbent article;
a backsheet on a garment-facing side of the absorbent article; and
an absorbent core positioned at least partially between the topsheet and the backsheet;
wherein at least one of the topsheet or the backsheet comprises the nonwoven according to claim 1.

16. A nonwoven extending in a machine direction and a perpendicular cross-machine direction and comprising a pattern of thermal bonds according to the following:
a) the pattern comprises thermal bonds disposed in parallel rows, the rows having a pitch angle of from about 0.5° to about 10° relative to the machine direction or the cross-machine direction;
b) a bonding area of all the thermal bonds covers from about 17% to about 30% of the area of the nonwoven;
c) the pattern comprises larger elliptical shape bonds and smaller elliptical shape bonds having different individual areas, wherein at least some of the larger elliptical shape bonds are disposed in the parallel rows, wherein at least some of the smaller elliptical shape bonds are disposed in the parallel rows, wherein a ratio of the number of the smaller elliptical shape bonds to the number of the larger elliptical shape bonds is at least 1.5, and wherein at least some of the parallel rows of the smaller elliptical shape bonds are disposed between at least some of the parallel rows of the larger elliptical shape bonds; and
d) wherein the larger and smaller elliptical shape bonds have a major dimension measured along a major direction and a minor dimension measured along a minor direction perpendicular to the major direction, wherein at least some of the larger and smaller elliptical shape bonds have a major direction which is not oriented parallel to the machine direction, and wherein the larger and smaller elliptical shape bonds have different major directions.

17. The nonwoven according to claim 16, having a basis weight ranging from about 10 gsm to 20 gsm and an opacity index of from about 15% to about 50%, wherein a row of smaller elliptical shape bonds is positioned intermediate two parallel rows of larger elliptical shape bonds, and wherein the distance between two adjacent parallel rows of the larger elliptical shape bonds is from about 2.0 mm to about 8 mm and a distance center-to-center for at least some of the larger elliptical shape bonds in the same parallel row ranges from about 2 mm to about 8 mm.

18. An absorbent article comprising:
a topsheet on a wearer-facing side of the absorbent article;
a backsheet on a garment-facing side of the absorbent article; and
an absorbent core positioned at least partially between the topsheet and the backsheet;
wherein at least one of the topsheet or the backsheet comprises the nonwoven according to claim 17.

19. A nonwoven extending in a machine direction and a perpendicular cross-machine direction and comprising a pattern of thermal bonds according to the following:
a) the pattern comprises thermal bonds disposed in parallel rows, the rows having a pitch angle of from about 0.5° to about 15° relative to the cross-machine direction;
b) a bonding area of all the thermal bonds covers from about 17% to about 30% of an area of the nonwoven;
c) the pattern comprises larger elliptical shape bonds and smaller elliptical shape bonds having different individual areas, wherein at least some of the larger elliptical shape bonds are disposed in the parallel rows, wherein at least some of the smaller elliptical shape bonds are disposed in the parallel rows, wherein a ratio of the number of the smaller elliptical shape bonds to the number of the larger elliptical shape bonds is at least 1.5, and wherein at least some of the parallel rows of the smaller elliptical shape bonds are disposed between at least some of the parallel rows of the larger elliptical shape bonds; and
d) wherein the smaller and larger elliptical shape bonds have a major dimension measured along a major direction and a minor dimension measured along a minor direction perpendicular to the major direction, wherein at least some of the smaller and larger elliptical shape bonds have a major direction which is not oriented parallel to the machine direction, and wherein the smaller and larger elliptical shape bonds have different major directions;
wherein a the bonding area of all the thermal bonds ranges from about 19% to about 28% of an area of the nonwoven; and
wherein the smaller elliptical shape bonds have an individual area of less than 1.5 mm$^2$, and wherein the larger elliptical shape bonds have an individual area of at least 1.5 mm$^2$.

20. An absorbent article comprising:
a topsheet on a wearer-facing side of the absorbent article;

a backsheet on a garment-facing side of the absorbent article; and an absorbent core positioned at least partially between the topsheet and the backsheet;

wherein at least one of the topsheet or the backsheet comprises the nonwoven according to claim 19.

\* \* \* \* \*